(12) United States Patent
Sjolund (10) Patent No.: US 10,946,215 B2
(45) Date of Patent: Mar. 16, 2021

(54) RADIOTHERAPY PLANNING SYSTEMS

(71) Applicant: Elekta AB (publ), Stockholm (SE)

(72) Inventor: Jens Sjolund, Stockholm (SE)

(73) Assignee: Elekta AB (publ), Stockholm (SE)

( * ) Notice: Subject to any disclaimer, the term of this patent is extended or adjusted under 35 U.S.C. 154(b) by 313 days.

(21) Appl. No.: 15/780,782

(22) PCT Filed: Dec. 2, 2016

(86) PCT No.: PCT/EP2016/079560
§ 371 (c)(1),
(2) Date: Jun. 1, 2018

(87) PCT Pub. No.: WO2017/093469
PCT Pub. Date: Jun. 8, 2017

(65) Prior Publication Data
US 2020/0246635 A1    Aug. 6, 2020

(30) Foreign Application Priority Data

Dec. 4, 2015 (GB) ..................................... 1521438

(51) Int. Cl.
*A61N 5/10* (2006.01)
(52) U.S. Cl.
CPC .......... *A61N 5/1031* (2013.01); *A61N 5/1039* (2013.01); *A61N 5/1001* (2013.01); *A61N 5/1084* (2013.01)
(58) Field of Classification Search
CPC ............................................ A61N 5/10–1084
See application file for complete search history.

(56) References Cited

U.S. PATENT DOCUMENTS

| | | | | |
|---|---|---|---|---|
| 2006/0274924 A1* | 12/2006 | West | ...................... | A61N 5/103 382/131 |
| 2011/0255665 A1* | 10/2011 | Breedveld | ............ | A61N 5/1038 378/65 |
| 2012/0123184 A1* | 5/2012 | Otto | ...................... | A61N 5/1067 600/1 |

OTHER PUBLICATIONS

Holdsworth CH et al. Adaptive IMRT using a multiobjective evolutionary algorithm integrated with a diffusion-invasion model of glioblastoma.Phys. Med. Biol. 57 (2012) 8271-8283 (Year: 2012).*

(Continued)

*Primary Examiner* — Catherine B Kuhlman
(74) *Attorney, Agent, or Firm* — Finnegan, Henderson, Farabow, Garrett & Dunner, LLP

(57) ABSTRACT

Embodiments of the present disclosure are directed to treatment planning systems for a radiotherapy apparatus. In one implementation, a treatment planning system may include a computational processor configured to apply a set of instructions to an input data set. The input data set may include a three-dimensional dose distribution for delivery by the radiotherapy apparatus to a volume to be irradiated, a three-dimensional volume image characterizing tissue types within the volume to be irradiated, and a set of apparatus parameters which characterize the radiotherapy apparatus. The set of instructions may include a computational process configured to output a treatment plan for delivery of the dose distribution by the radiotherapy apparatus, by optimising a function representing a time-dependent response of the tissue types to an applied radiation.

18 Claims, 2 Drawing Sheets

(56) References Cited

OTHER PUBLICATIONS

International Search Report and Written Opinion dated Feb. 16, 2017, by the European Patent Office in PCT/EP2016/079560 (11 pages).
C.H. Holdsworth et al., "Adaptive IMRT using a multiobjective evolutionary algorithm integrated with a diffusion-invasion model of glioblastoma," Physics in Medicine and Biology, vol. 57 (24), pp. 8271-8283 (Dec. 2012).
C. P. South et al., "A theoretical framework for prescribing radiotherapy dose distributions using patient-specific biological information." Medical Physics, vol. 35 (10), pp. 4599-4611 (Oct. 2008).

* cited by examiner

RADIOTHERAPY PLANNING SYSTEMS

CROSS-REFERENCE TO RELATED PATENT APPLICATIONS

This application is a U.S. national stage entry under 35 U.S.C. § 371 of International Application No. PCT/EP2016/079560, filed Dec. 2, 2016, which claims the benefit of United Kingdom Patent Application No. 1521438.0, filed Dec. 4, 2015, both of which are hereby incorporated by reference in their entirety.

FIELD OF THE INVENTION

The present invention relates to the field of planning systems for radiotherapeutic use.

BACKGROUND ART

Radiotherapy apparatus delivers a beam of high-energy radiation which is directed towards a tumour site (or other lesion) in a collimated and controlled manner. A variety of devices are able to do so.

External-beam radiotherapy includes two main forms single-source radiotherapy and multi-source radiotherapy. In single-source radiotherapy, a beam of radiation (typically in the MeV range, apt to damage tumour cells) is generated by a linear accelerator or the like, and directed towards the patient. The source is movable so as to allow a range of irradiation directions to be chosen, and the lateral extent of the beam is limited by collimating elements so as to match a pattern determined in a predetermined treatment plan, such as the external profile of the tumour or a subsection of it. The direction of the beam is varied so that the tumour is irradiated from multiple directions, thereby reducing the dose delivered to tissue surrounding the tumour site.

Multiple-source external-beam radiotherapy uses a large number of fixed sources, often isotopic sources such as $^{60}Co$ which decays via a process including gamma emission. These are mounted in (typically) an approximately hemispherical collimator arrangement which collimates each source to direct its radiation to the centre of the hemisphere. Thus, at that centre point the radiation fluence is very high, whereas away from that point the fluence drops markedly. Individual sources can be blocked or opened to allow irradiation. A patient can therefore be positioned (with all sources blocked), and a selection of sources can then be opened for a specified time to create a high fluence at a specific location within the patient and deliver a specific dose. A tumour might be exposed to several "shots" (which may be at different locations) in order to fill up the target volume with the prescribed dose level. Also, several tumour sites can be treated in one treatment. An example is the Leksell Gamma Knife, supplied by the applicant.

Internal radiotherapy (known as brachytherapy) involves placing a sealed radiation source in or adjacent to the area requiring treatment. Radiation is then delivered directly to the lesion site. The principal form of control is obtained from the positioning of the source relative to the site, but the source strength parameters can also be controlled.

Radiotherapy treatment is often delivered in "fractions", i.e. individual fractional doses delivered at intervals of (for example) a day, which add up to a total dose to be delivered; delivering the dose in fractions alleviates the side-effects on the healthy tissue surrounding the tumour site. In multiple-source radiotherapy, the fractions may refer to successive shots.

Typically, a treatment plan will be drawn up prior to delivery of the first fraction, which will detail the nature of the dose delivery in terms of the operational steps to be taken by the radiotherapy apparatus. This will usually be specific to the apparatus in question; for example when using a multi-source stereotactic radiosurgery apparatus the plan will usually include details of the individual shots including which sources will be active and for how long. In the context of a dose delivered by a single-source linear accelerator device, the treatment plan might include beam shapes, directions, and intensity/duration of a number of beam segments that together will form the treatment fraction. A treatment plan for a brachytherapy treatment might include locations, orientations, dwell times and dose rates. These beam segments are designed to, collectively, deposit a three-dimensional dose distribution in the tumour which corresponds to that prescribed by a clinician, and which both generally minimises the dose delivered to non-tumour areas, and remains within upper dose limits for certain designated sensitive areas of the patient. This is a challenging problem, and the treatment plan is generally arrived at by an iterative process carried out on a computational device. Such iterative processes take as their initial boundary conditions the three-dimensional dose that is to be delivered (divided by the number of fractions) and the constraints of the radiotherapy apparatus that is to be used in delivery and use computational methods to derive a treatment plan. The patient then attends for the set number of fractions and the fractional dose is delivered each time according to the treatment plan.

Progress in radiation oncology has always been closely linked with innovations in medical radiation physics and computer sciences, morphological, and functional imaging methodologies, and new insights into the radiobiology and radiopathophysiology of both tumours and normal tissues at the molecular, cellular, and tissue level. During the last two decades significant advances have been made in medical imaging (e.g., hybrid imaging devices) of both anatomy and physiology, and in medical radiation physics (i.e., beam generation and shaping, ion beam therapy) as well as in computer sciences. These advances have made it possible to define target structures and volumes of radiotherapy with increasing precision and to deliver radiation doses with unprecedented accuracy to the predefined target, which includes both the macroscopic tumour and the region of assumed microscopic spread.

Based on the high spatial resolution of the morphological/anatomical imaging data, sophisticated treatment techniques such as intensity modulated radiotherapy (IMRT), stereotactic radiotherapy or even ion beam therapy can be planned and executed. During the last decade equipment and hybrid tools for image-guided radiotherapy (IGRT) have been developed, such as the linear accelerator with CT. Ongoing developments like the hybrid MR linear accelerator will allow visualizing structures during treatment with an outstanding soft tissue contrast. Besides geometric accuracy and temporal variations during treatment delivery, the biological aspects and their temporal variation add another level of complexity in cancer management (Ling, 2000).

SUMMARY OF THE INVENTION

The established radiotherapy treatment planning protocols therefore treat a cancer as a fixed entity, defined within a "target volume". Some modulation of this idea is allowed via the concept of dose painting, in which specified areas of the target are singled out (such as low-$O_2$ volumes), but the basic concept is still that the target volume is a fixed shape, as are the OAR ("organ at risk") volumes around it. The focus has been on faster or more accurate planning processes and more accurate or reliable delivery methods.

However, a cancer is (literally) a living thing and changes over time. It also has time-dependent responses to external influences (such as radiotherapy), and may have a degree of tumour heterogeneity. In the present invention, we propose to take such responses into account in the treatment planning stage, in order to allow a treatment plan to be arrived at which is better able to treat the tumour in question.

The present invention therefore proposes a treatment planning system for a radiotherapy apparatus comprising a computational processor applying a set of instructions to an input data set, the input data set comprising a dose distribution which is to be achieved by the radiotherapy apparatus within a volume to be irradiated, a three-dimensional volume image characterising the tissue types within the volume to be irradiated, and a set of process parameters which characterise a radiotherapy delivery process, with the set of instructions including an iterative computational process arranged to output a treatment plan apt to deliver the three-dimensional dose distribution when implemented by the delivery process, by optimising a function that includes at least one part representing a time-dependent response of the tissue types to an applied radiation.

Treatment plan optimization is often (especially for linear accelerator-based systems) divided into two phases; a first phase in which an idealized version of the optimization problem is solved (e.g. as a "fluence map optimization") and a second phase in which the solution of the idealized problem is converted into actual machine parameters by solving another optimization problem. In the present invention, the steps might be first to find the ideal 4D dose distribution, and then find machine parameters that attempt to realise this 4D dose distribution. In other words, it is likely to be more effective to apply the present invention on the above-described first phase. However, single-phase optimization is still possible, in which the treatment response is optimized with the machine parameters as additional degrees of freedom or constraints (sometimes referred to as "direct machine parameter optimization").

The input data set can further comprise a number of treatment fractions over which the dose distribution is to be delivered. The set of instructions can then include a fractional distribution step arranged to assign fractional parts of the dose distribution to successive treatment fractions, taking into account time- and dose-dependent characteristics of the tissue types within the volume image, and the iterative computational process can then be arranged, for each nonidentical fraction, to take into account the fractional part of the dose distribution and the set of apparatus parameters, to derive a set of treatment instructions apt to deliver the fractional part when carried out by the radiotherapy apparatus.

The three-dimensional volume image will ideally characterise the tissue types according to at least their local chemical composition and related factors, to reflect (within the tumour areas) the tumour microenvironment and assist in modelling the dose response.

The optimisation function can include terms representing time-dependent responses such as a cell repair model and a tumour diffusion model.

BRIEF DESCRIPTION OF THE DRAWINGS

An embodiment of the present invention will now be described by way of example, with reference to the accompanying figures in which.

DETAILED DESCRIPTION OF THE EMBODIMENTS

Observations show us that cancers are complex, evolving, multiscale systems that are characterized by profound spatial and temporal heterogeneity in their biologic characteristics. Many of the biologic aberrations of cancer can be imaged in vivo with no or minimal tissue disruption; functional imaging techniques can now depict these processes at the tumour level, in peritumoural regions, and at the organ and whole organism levels. Many key cancer hallmarks can be mapped, including deregulated tumour cell proliferation, angiogenesis, metastasis, apoptosis, and the consequences of altered metabolism.

Current dose prescription schemes generally employ a radiation dose together with a fractionation scheme according to which the dose is spread over a number of fractions delivered at regular intervals, e.g. on a daily basis. The actual prescription in a specific case is of course dependent on the target type (often a tumour, but may be an alternative such as a functional target). A conventional treatment protocol consists of five fractions a week for a 6-7 week period. In each (identical) fraction, a dose of 1.8-2.0 Gy is delivered. The dose-per-fraction is given simply as the total prescription dose divided by the number of fractions. Variations on this fractionation scheme include:

1. Accelerated fractionation: a shortening of the overall treatment duration by giving two or three fractions per day but using similar total dose per fraction as conventional fractionation.

2. Hyperfractionation: an increase in the number of fractions, giving two or three fractions per day, with smaller doses per fraction than conventional, to yield a higher total dose but delivered over the same overall time as a conventional fractionation scheme.

3. Accelerated hyperfractionation: a greater number of fractions, each of a smaller fraction size, spread over a shorter overall treatment duration than a conventional fractionation scheme.

Modern functional imaging techniques allow the identification of subvolumes of tissue and organs related to specific morbidity symptoms and endpoints. These subvolumes often have different radiobiological characteristics, such as dose response, fractionation effect and cell repair times. Such imaging techniques define biological rather than anatomic targets. Furthermore, functional imaging allows the selection of sub-volumes, for example poorly oxygenated areas, for dose escalation. The selective boosting of the dose that is delivered to radio-resistant subvolumes is usually referred to as "dose painting". A range of "brushes" can be utilized, ranging from brachytherapy approaches to delivery methods with high-energy photon beams or ion beams. The application of dose painting is currently seen as being limited purely by the quality of relevant quantitative information from functional imaging; the problem that is currently being addressed is the improvement of the level of detail in that information so that the regions in need of escalation can be identified more accurately. Dose painting, as thought of today, thus refers to the tailoring of a spatially heterogeneous dose distribution to reflect the underlying radiobiological characteristics.

Another variation on the fractionation schemes mentioned earlier is "concomitant boosting", which has been proven more effective for some types of cancer. Concomitant boost schedules are characterized by delivering the boost (10-12 fractions) as second daily treatments during rather than following a basic wide field irradiation. The boost is directed at a sub region of the target, and thus constitutes a simple form of dose painting.

We have realised that these various techniques fail to adequately capture that cancerous tissues (as well as healthy tissues) have both a profound temporal as well as spatial heterogeneity in their biologic characteristics. To further improve the effectiveness of dose painting techniques, we therefore propose that time should be factored into the treatment planning stage. In other words, instead of simply highlighting specific areas for a higher dose rate, one should consider the temporal variations and the time-dynamics of the tissues in question as part of the treatment planning process. The time-dynamics may stem from one of several reasons, such as the innate tissue properties, the tissue's response to irradiation, or external factors such as medication or injection with e.g. radiosensitizers.

This could have implications both in the intra-fraction and the inter-fraction delivery of radiation. The intra-fraction aspect may be of particular relevance in multi-source (e.g. Leksell Gamma Knife) treatments or brachytherapy, where the time over which the irradiation is delivered can be significant, and biological repair mechanisms thus come into play. Such effects have been considered to some extent before, but then assuming a constant and spatially homogenous repair rate.

Concerning the inter-fraction delivery, the different time-scales of cell mechanisms such as cell proliferation and repair mean that it might be beneficial to divide the treatment into a set of unequal fractions. In the Gamma knife case, such a fractionation might in fact facilitate dose delivery, since the number of different shots in each session can be reduced, thereby lowering unwanted shutter dose.

In either of these cases, additional benefits can be expected if this type of treatment planning is combined with an accurate modelling of the underlying biological mechanisms and their interaction with the treatment. In this respect, the linear-quadratic (LQ) model is the most commonly used model for radiation-induced cell killing. Radiation induced reproductive cell death has been conclusively linked to DNA damage, specifically to DNA double-strand breaks. In cellular environment, double-strand break dose-response is linear up to doses of about 40 to 50 Gy and approximately 40 to 50 double-strand breaks are produced per Gy. Most double-strand breaks are faithfully repaired; however, some undergo binary misrepair, which may lead to a production of a lethal lesion, while some fail to get repaired. Induction, repair, and misrepair of double-strand breaks and formation of lethal lesions as a function of dose rate and time can be modelled mathematically as a system of differential equations. However, the resulting solutions are not in practice helpful; in the general case they are too complex and the special cases where the solutions are simple are not applicable to realistic scenarios. For doses and dose rates of relevance to radiation therapy, with a possible exception of doses per fraction in excess of 10 Gy per fraction, the yield of lethal lesions can be well approximated by an linear-quadratic (LQ) function of dose. That is, the fraction S of cells surviving irradiation by a dose d in n fractions can be approximated as $$S = e^{\left(-\alpha d - \beta \frac{d^2}{n}\right)}$$

where $\alpha$ and $\beta$ are proportionality constants. The effects of repopulation and repair can be reflected as additional terms within the exponent, for greater accuracy. Moreover, it can be shown that cell population susceptibility based on increased radio-sensitivity in the G2 and mitosis phases of the cell cycle can be incorporated into the model derivation without formal change.

The validity of the LQ model for large doses per fraction encountered in radiosurgery and stereotactic body radiation treatments (SBRT) is a subject of ongoing debate. Nevertheless, the LQ model of radiation-induced cell killing is the model that, for now at least, is considered best at providing a rational basis for comparisons between different regimens of treatment. As and when other models are developed, these could be used in substitution for the LQ model.

In a nutshell, the present invention introduces an additional degree of freedom in the treatment planning, in the form of time-dependent responses of the tissue types involved. Although the objective of the treatment remains the same—local control of the target with minimal side effects on healthy tissue—we propose to achieve this not just by prescribing a total dose at each spatial location but by considering the dose (or equivalently dose-rate) as a function of time at each spatial location. In mathematical terms, this means that we strive to optimize a functional rather than a function.

This is a new general approach to treatment planning in the field of radiotherapy. To illustrate this, we will consider a number of examples.

Example 1

Time-Dependent Modelling

The growth of gliomas, a type of brain cancer, can be modelled as a reaction-diffusion type partial differential equation. Such a model has also been extended to incorporate the effect of radiation treatment. Let c(x,t) denote the concentration of tumour cells at location x (three dimensional) and time t. The time evolution of the concentration can then be determined from the partial differential equation:

$$\frac{\partial c}{\partial t} = \nabla \cdot D(x,t) \nabla c + \rho(x,t) c - R(x,t,d(x,t)) c$$

where D(x,t) is a (possibly space- and time-varying) diffusion tensor, p(x,t) is the net rate of proliferation and R(x,t,d(x,t)) represents the effect of radiotherapy (which could be modelled using the LQ model, for example). Whatever the model of the treatment effect, we consider it being a function of parameters (e.g. intrinsic radioresistance, oxygenation, repair rates, concentration of pharmaceuticals, cell cycle phase) that may have both a spatial and temporal dependence.

If we define the right hand side of the above partial differential equation as f(x,t,d(x,t),c(x,t)) we can formally integrate it to find the concentration of tumour cells at time T $$c(x,T) = c(x,0) + \int_0^T f(x,t,d(x,t),c(x,t)) dt.$$

If the treatment objective is to, say, have as few surviving tumour cells at time T as possible means that we want to minimize the functional $$J[d(x,t)] = \iiint_{volume} c(x,T)dx = \iiint_{volume} \left( c(x,0) + \int_0^T f(x,t,d(x,t),c(x,t))dt \right) dx$$

This is however just one possible choice of the functional to optimize.

Example 2

Temporal Dose Painting with Molecular Imaging Data

There is a known link between the microenvironment of a cell and its surrounding and the effect of radiotherapy; for example, an ample supply of nutrients allows the tumour to grow faster (e.g. due to increased cell proliferation) and may increase the repair rate. It is also well established that low oxygen levels make cells more resistant to radiation. Molecular imaging (also known as functional imaging or physiological imaging) techniques such as positron emission tomography (PET), functional magnetic resonance imaging (fMRI), dynamic contrast enhanced computed tomography (DCE-CT) and magnetic resonance spectroscopy (MRS) allows direct imaging of the local chemical composition. This imaging can be done either during treatment (online) or not (offline). Online imaging is achievable with systems such as a combined MR and linear accelerator, or a radiosurgery system equipped with X-ray imaging capabilities. The information as to chemical composition can then be used to design a treatment plan that maximizes the treatment effect, e.g. by having spatially varying fractionation schemes or using different dose rates in different parts of the target.

Figure 1:
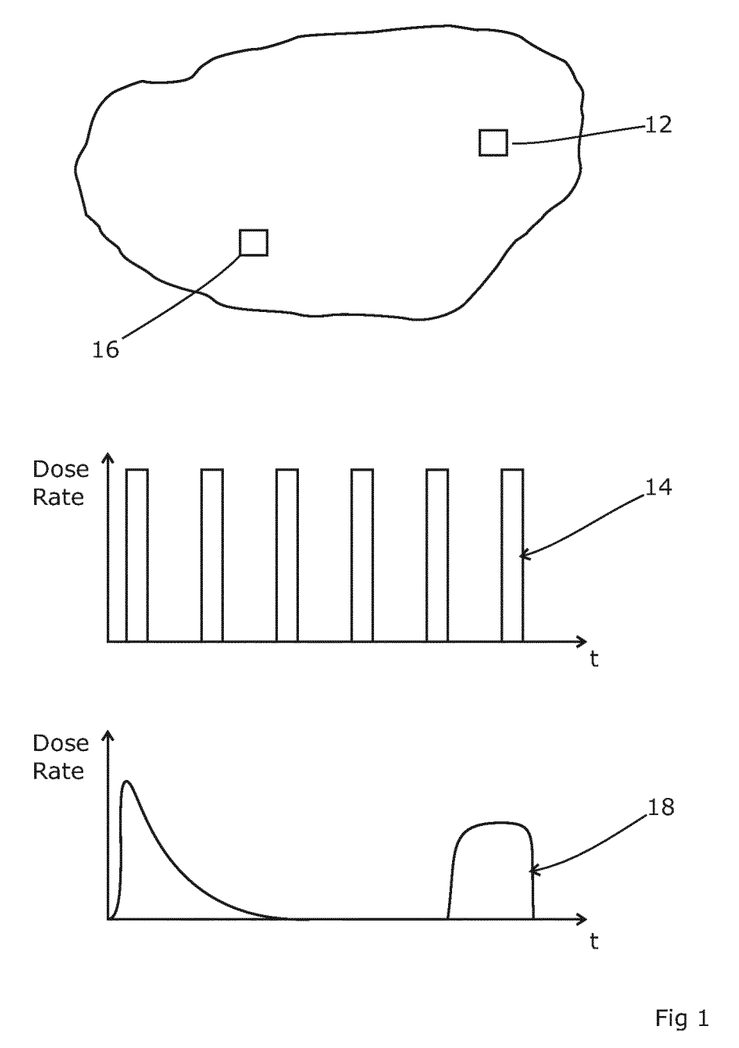
FIG. 1 illustrates a treatment plan with spatially-varying dose/time profiles.

This is illustrated in FIG. 1. Information provided by molecular imaging is used to yield a more optimal treatment plan that includes different dose rates and temporal characteristics. Within the overall target volume 10, one sub-region 12 has the dose rate vs time profile 14 consisting of a series of spaced brief high-dose-rate bursts. Meanwhile, a second sub-region 16 has the dose rate vs time profile 18 consisting of an initially high dose rate that tails off to zero, followed by a moderate dose delivered toward the end of the fraction. Naturally, the precise pattern will be dependent on the characteristics of the tumour in question. An online imaging system will allow online adaptation of the treatment to maximize treatment effect.

Example 3

Inter-Fraction Modulation—Unequal Fractions

Concerning the inter-fraction delivery, the different timescales of cell mechanisms such as cell proliferation and repair mean that it might be beneficial to divide the treatment into a set of unequal fractions. As an example, suppose that a target has an exceedingly high repair rate, on par with the rate of cell killing at low dose rates. Thus, irradiation at low dose rate would have substantially no effect. To be successful, the treatment should instead strike a swift and killing blow to one region of the target at the time. In the Gamma knife case, such a fractionation would even facilitate dose delivery, since the number of different shots in each session can be reduced, thereby lowering unwanted shutter dose.

Figure 2:
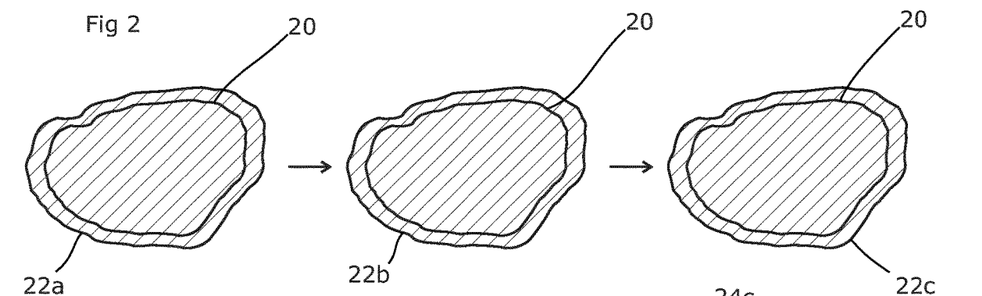
FIGS. 2 and 3 compare an equal-fractions treatment plan with a varying-fraction treatment plan.
Figure 3:
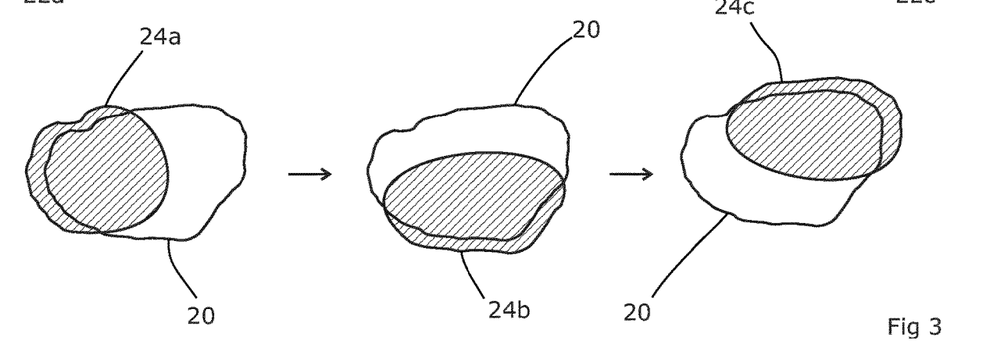

This is illustrated in FIGS. 2 and 3, which illustrate a treatment of a tumour volume 20 in three fractions. FIG. 2 shows the conventional approach of equal fractions 22a, 22b, 22c delivered at spaced intervals such as a day. Each covers substantially all of the tumour site 20 plus a margin around the tumour that is dictated by the expected tumour volume growth and the delivery apparatus accuracy and resolution. FIG. 3 shows the proposed approach, whereby the same total dose is delivered in three unequal fractions 24a, 24b, 24c. Each is smaller in volume than the equal fractions of FIG. 2, but the overall dose delivered by the fractionated treatment is the same. Thus, the dose per unit volume of each fraction is higher, and the resulting death rate of tumour cells within the treated volumes can be expected to be higher. The subsequent repair rate will then be insufficient to allow the tumour to recover to the same extent as would be observed using equal identical fractions.

This could be achieved in practice by allowing the treatment planning algorithm additional degrees of freedom in shaping the individual fraction doses, including the dose-dependent cell death rates and time-dependent effects of repair, recovery (etc) within the algorithm, and setting as the tumour end-state as a factor to be optimised.

Example 4

Intra-Fraction Modulation

A variation of the previous example is when the temporal characteristics of the dose rate are considered in the course of a single treatment session. The intra-fraction aspect may be of particular relevance in Gamma knife treatments or brachytherapy, where the time of irradiation can be significant and biological repair mechanisms thus come into play. Such effects have been considered to some extent before, but then assuming a constant and spatially homogenous repair rate.

Example 5

Tumour Heterogeneity, Including Spatially Varying Tumour Grade

Tumour grade is the description of a tumour based on how abnormal the tumour cells and the tumour tissue look under a microscope. It is an indicator of how quickly a tumour is likely to grow and spread. If the cells of the tumour and the organization of the tumour's tissue are close to those of normal cells and tissue, the tumour is called "well-differentiated." These tumours tend to grow and spread at a slower rate than tumours that are "undifferentiated" or "poorly differentiated," which have abnormal-looking cells and may lack normal tissue structures. Based on these and other differences in microscopic appearance, pathologists assign a numerical grade to most cancers. The factors used to determine tumour grade can vary between different types of cancer.

Tumour grading is typically done by microscopy of histology samples acquired from a biopsy of the tumour, but it is also possible to use non-invasive imaging for tumour grading. A significant drawback of assessments based on a biopsy is that it only samples a very small part of the tumour. It has been established that some tumour types, notably glioblastoma multiforme, may have different grades in different parts of the tumour. The treatment should of course be adapted to these variations, with a more aggressive treatment of regions where the tumour is aggressive (high grade).

Other forms of tumour heterogeneity can also be dealt with in a corresponding manner.

Example 6

Spatially Varying Diffusion Tumour Growth

As noted in the discussion of the mathematical basis of 4D dose painting (above), the tumour growth can in some cases be modelled using a diffusion type partial differential equation. The diffusion tensor (that reflects the expected spread of the tumour) can be estimated either from longitudinal scans of arbitrary kind, but it could also be measured directly using diffusion MRI techniques such as diffusion tensor imaging (DTI). Equipped with this knowledge of how the tumour is likely to spread, and thereby also implicitly about the microscopic invasion not yet visible, the treatment plan could be adapted accordingly.

Figure 4:
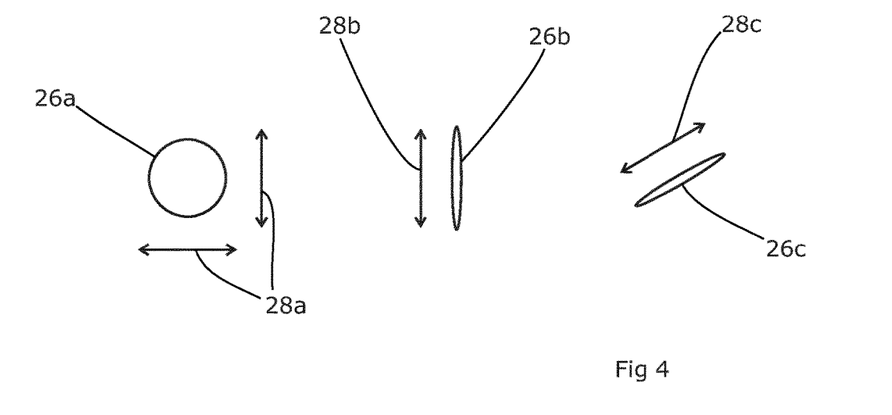
FIG. 4 shows how diffusion characteristics can be taken into account in a treatment plan.

FIG. 4 shows an illustration of this idea. The ellipsoids 26a, 26b, 26c represent the diffusion tensors at different positions at a particular instance in time. The arrows 28a, 28b, 28c represent the likely directions of tumour spread which can be inferred from the diffusion tensor images. An optimal treatment plan should be adapted accordingly. In these examples the avenues of growth could merit separate treatment considerations; it is conceivable that irradiation would best be delivered along the direction of the arrows so that the dose delivered to nominally healthy areas would in fact assist in treating not-yet-observed spread of the tumour.

Again, this example simply requires the time-dependent characteristics of the tumour to be taken into account during the treatment planning process, so that the treatment is optimised towards the expected evolution of the tumour rather than its currently observed shape.

Example 7

Timing Irradiation with Radiosensitizer/Drug Uptake

Radiosensitizers such as high-Z nanoparticles have been found to locally boost the radiation dose delivered to the tissue. There exists various ways of administering the radiosensitizers, injection and inhalation being two variants. Regardless, the uptake of these has a well-defined temporal aspect, analogous to how the arterial input function (AIF) describes the perfusion of contrast fluid in dynamic contrast enhanced image acquisition (using CT, MRI or some other modality) governs the contrast uptake. Typical time-scales are on the order of seconds to minutes, i.e. at the intra-fraction level. To get the maximum effect out of the radiosensitizers, it is imperative to deliver radiation in sync with the radiosensitizer concentration. In some instances it might be possible that the radiosensitizer (or substance of interest) can be imaged directly, e.g. if it has the right type of radioactive decay it could be imaged using single photon emission computed tomography (SPECT) or positron emission tomography (PET); another case would be it has sufficient concentration to be detectable using magnetic resonance spectroscopy (MRS).

On the longer, inter-fraction timescale, it may also be desirable to attempt to leverage synergies with other pharmaceuticals, e.g. chemotherapy or anti-angiogenic drugs such as Bevacizumab. Mutations that lead to EGFR over-expression or overactivity have been associated with a number of cancers, including lung cancer, anal cancers and glioblastoma multiforme. These somatic mutations involving EGFR lead to its constant activation, which produces uncontrolled cell division. Another conceivable application is thus the combination with an Epidermal growth factor receptor (EGFR) inhibitor, such as Cetuximab.

Example 8

Automatic Temporal Reordering of Dose Delivery

Since current practice does not take the temporal degree of freedom into account, the intra-fraction order in which the dose is delivered is arbitrary (or more likely dictated by the treatment machine's convenience). In today's clinical practice, the treatment plan quality is only evaluated based on the total dose in a fraction, which means that it should be possible to reorder the dose delivery to achieve maximum treatment efficacy within the confines of current practice. A clinician could thus plan the treatment in the same manner as before and then, optionally, an automatic procedure could handle the temporal degree of freedom. Thus, the same total dose could be delivered, but with a higher degree of efficiency.

Solution Methods

Generally, the optimisation process simply requires additional degrees of freedom to be incorporated, with the algorithm modelling the temporal effect of the delivered doses and including a measure of quality that is to be optimised which reflects the final state of the tumour after the dose has been applied.

This could be achieved via an open-loop controller (also known as a non-feedback controller), which is a type of controller that computes its input into a system using only the current state and its model of the system. In our case, this would correspond to having a model such as that of tumour growth and treatment effect above, which is obtained before the treatment course is initiated. This model can be based on input from any of the multitude of sources mentioned before. The state of the system would in this case be the full specification of the tumour properties and the radiation apparatus. The control variable is basically the four dimensional dose delivery.

In an open-loop setting, the state of the system is assumed to evolve precisely according to the predictions of the model. This allows a full specification of an optimization problem, e.g. using what is referred to as direct or indirect methods. An indirect method directly optimizes the functional of interest by e.g. forming the augmented Hamiltonian and solving the resulting dynamical system. In a direct method the state and/or control variables are approximated using an appropriate function approximation (e.g., polynomial approximation or piecewise constant parameterization). Simultaneously, the cost functional is approximated as a cost function. Then, the coefficients of the function approximations are treated as optimization variables whereby the problem is "transcribed" to a standard nonlinear optimization problem.

Alternatively, a closed-loop system can be employed, i.e. one in which the system receives feedback during the course of the treatment, and may be adjusted accordingly. This is then referred to as a closed-loop control. The type of feedback may in general involve any of the inputs mentioned before but as an example consider e.g. tissue oxygenation, portal dosimetry or tumor response assessed from imaging biomarkers. Note in particular that the type of feedback is not limited to patient properties, it could also be external factors such as how the patient has been positioned in earlier treatment sessions or how the patient is moving in the ongoing treatment session, as assessed from intra-fraction motion management system that could use e.g. infra red (IR) tracking, MRI, CBCT, planar X-ray imaging, laser tracking, ultrasound or respiratory measurements.

Optimal control of closed-loop system is the subject of a field called optimal control theory. Two of the most prominent methods that could be applied to the problem at hand are dynamic programming and model predictive control.

Data Sources

The model data may include information such as imaging data (e.g., MRI, CT, X-ray, PET, SPECT, and the like), organ or volume of interest segmentation data, functional organ modelling data (e.g., serial versus parallel organs, and appropriate dose response models), radiation dosage (e.g., also including dose-volume histogram (DVH) information), lab data (e.g., hemoglobin, platelets, cholesterol, triglycerides, creatinine, sodium, glucose, calcium, weight), vital signs (blood pressure, temperature, respiratory rate and the like), genomic data (e.g., genetic profiling), demographics (age, sex, ethnicity), other diseases affecting the patient (e.g., cardiovascular disease, respiratory disease, diabetes, radiation hypersensitivity syndromes, and the like), medications and drug reactions, diet and lifestyle (e.g., smoking or non-smoking), environmental risk factors, tumour characteristics (histological type, tumour grade, hormone and other receptor status, tumour size, vascularity cell type, cancer staging, Gleason score), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP, and the like), single nucleotide polymorphisms (SNP) analysis (e.g., XRCC1, XRCC3, APEX1, MDM2, TNFR, MTHFR, MTRR, VEGF, TGFβ, TNFα), and the like.

It will of course be understood that many variations may be made to the above-described embodiment without departing from the scope of the present invention.

The invention claimed is:

1. A radiotherapy system for treatment planning the radiotherapy system comprising:
    a radiotherapy apparatus configured to irradiate a target volume; and
    a computational processor configured to apply a set of instructions to an input data set, the input data set including:
        a dose distribution for the target volume, wherein the dose distribution is configured to be delivered by the radiotherapy apparatus,
        a three-dimensional volume image characterizing tissue types within the target volume, and
        a set of apparatus parameters which characterize the radiotherapy apparatus,
    wherein the computational processor is configured to execute the set of instructions to:
        optimize a function representing a time-dependent response of the tissue types within the target volume to the dose distribution,
        derive a four-dimensional dose distribution for the target volume based on the optimized function, wherein for each tissue type within the target volume, the four-dimensional dose distribution characterizes a tissue-specific timing pattern for radiation dose delivery to the tissue type,
        generate a treatment plan for the radiotherapy apparatus based on the four-dimensional dose distribution and the set of apparatus parameters, and
        control the radiotherapy apparatus to irradiate the target volume based on the generated treatment plan.

2. The radiotherapy system of claim 1,
    wherein the input data set includes treatment fraction data indicating at least one treatment fraction over which the dose distribution is configured to be delivered to the target volume, and
    wherein the computational processor is further configured to execute the set of instructions to:
        perform a fractional distribution step to assign non-identical fractional parts of the dose distribution to successive treatment fractions, wherein the assignment is based on time- and dose-dependent characteristics of the tissue types within the volume image; and
        control the radiotherapy apparatus to deliver the non-identical fractional parts of the dose distribution to the target volume.

3. The radiotherapy system of claim 1, wherein the three-dimensional volume image characterizes the tissue types of the target volume based on local microenvironments of the tissue types.

4. The radiotherapy system of claim 1, wherein the computational processor is configured to execute the set of instructions to:
    optimize the function representing the time-dependent response of the tissue types without reference to the set of apparatus parameters; and
    further optimize the four-dimensional dose distribution in view of the set of apparatus parameters to generate the treatment plan for the radiotherapy apparatus.

5. The radiotherapy system of claim 1, wherein the function representing the time-dependent response of the tissue types represents at least one of a cell repair model or a tumor diffusion model.

6. The radiotherapy system of claim 1, wherein the computational processor is configured to execute the set of instructions to perform an iterative computational process to generate the treatment plan for the radiotherapy apparatus.

7. A method of producing a treatment plan for a radiotherapy apparatus, the method comprising:
    generating an input data set including:
        a dose distribution for a target volume to be irradiated, wherein the dose distribution is configured to be delivered by the radiotherapy apparatus,
        a three-dimensional volume image characterizing tissue types within the target volume, and
        a set of apparatus parameters which characterize the radiotherapy apparatus;
    generating a treatment plan for delivery of the dose distribution by:
        optimizing a function representing a time-dependent response of the tissue types within the target volume to the dose distribution,
        deriving a four-dimensional dose distribution for the target volume based on the optimized function, wherein for each tissue type within the target volume, the four-dimensional dose distribution characterizes a tissue-specific timing pattern for radiation dose delivery to the tissue type, and generating the treatment plan based on the four-dimensional dose distribution and the set of apparatus parameters; and controlling the radiotherapy apparatus to irradiate the target volume based on the generated treatment plan.

8. The method of claim 7,
wherein the input data set includes treatment fraction data indicating at least one treatment fraction over which the dose distribution is configured to be delivered to the target volume, and
wherein the method further comprises:
performing a fractional distribution step to assign non-identical fractional parts of the dose distribution to successive treatment fractions, wherein the assignment is based on time- and dose-dependent characteristics of the tissue types within the volume image; and
controlling the radiotherapy apparatus to deliver the non-identical fractional parts of the dose distribution to the target volume.

9. The method of claim 7, wherein the three-dimensional volume image includes data characterizing the tissue types of the target volume based on local microenvironments of the tissue types.

10. The method of claim 7, further comprising:
optimizing the function representing the time-dependent response of the tissue types without reference to the set of apparatus parameters; and
further optimizing the four-dimensional dose distribution in view of the set of apparatus parameters to generate the treatment plan for the radiotherapy apparatus.

11. The method of claim 7, wherein the function representing the time-dependent response of the tissue types represents at least one of a cell repair model or a tumor diffusion model.

12. The method of claim 7, wherein generating the treatment plan for the radiotherapy apparatus is an iterative computational process.

13. A treatment planning apparatus, comprising:
a data storage element configured to store an input data set, the input data set including:
a dose distribution for a target volume to be irradiated, wherein the dose distribution is configured to be delivered by a radiotherapy apparatus,
a three-dimensional volume image characterizing tissue types within the target volume, and
a set of apparatus parameters which characterize the radiotherapy apparatus; and
a computational processor programmed to apply a set of instructions to the input data set, the computational processor being programmed to execute the set of instructions to:
optimize a function representing a time-dependent response of the tissue types within the target volume to the dose distribution,
derive a four-dimensional dose distribution for the target volume based on the optimized function, wherein for each tissue type within the target volume, the four-dimensional dose distribution characterizes a tissue-specific timing pattern for radiation dose delivery to the tissue type,
generate a treatment plan for the radiotherapy apparatus based on the four-dimensional dose distribution and the set of apparatus parameters, and
control the radiotherapy apparatus to irradiate the target volume based on the generated treatment plan.

14. The treatment planning apparatus of claim 13,
wherein the input data set includes treatment fraction data indicating at least one treatment fraction over which the dose distribution is configured to be delivered to the target volume, and
wherein the computational processor is further configured to execute the set of instructions to:
perform a fractional distribution step to assign non-identical fractional parts of the dose distribution to successive treatment fractions, wherein the assignment is based on time- and dose-dependent characteristics of the tissue types within the volume image; and
control the radiotherapy apparatus to deliver the non-identical fractional parts of the dose distribution to the target volume.

15. The treatment planning apparatus of claim 13, wherein the three-dimensional volume image characterizes the tissue types of the target volume based on local microenvironments of the tissue types.

16. The treatment planning apparatus of claim 13, wherein the computational processor is configured to execute the set of instructions to:
optimize the function representing the time-dependent response of the tissue types without reference to the set of apparatus parameters; and
further optimize the four-dimensional dose distribution in view of the set of apparatus parameters to generate the treatment plan for the radiotherapy apparatus.

17. The treatment planning apparatus of claim 13, wherein the function representing the time-dependent response of the tissue types represents at least one of a cell repair model or a tumor diffusion model.

18. The treatment planning apparatus of claim 13, wherein the computational processor is configured to execute the set of instructions to perform an iterative computational process to generate the treatment plan for the radiotherapy apparatus.

* * * * *